United States Patent [19]
Noda

[11] 4,007,630
[45] Feb. 15, 1977

[54] DEVICE FOR DETECTING DAMAGE ON ROTATORS
[75] Inventor: Banda Noda, Tokyo, Japan
[73] Assignee: Nippon Seiko K.K., Tokyo, Japan
[22] Filed: July 9, 1975
[21] Appl. No.: 594,251
[30] Foreign Application Priority Data
July 12, 1974    Japan .............................. 49-79111
[52] U.S. Cl. ................................................. 73/71.4
[51] Int. Cl.² ................ G01M 13/04; G01M 15/00
[58] Field of Search ...................... 73/67, 71.2, 71.4
[56] References Cited
UNITED STATES PATENTS

| 2,496,337 | 2/1950  | de Boisblanc ......................... 73/35 |
| 3,913,084 | 10/1975 | Bollinger et al. ................... 73/71.4 |

Primary Examiner—James J. Gill
Attorney, Agent, or Firm—Shapiro and Shapiro

[57] ABSTRACT

There is disclosed a device for detecting damage on rotators or rotary bodies such as for example ball bearings having rolling elements. A mechanical vibration or sound produced periodically due to damage on the rotator when it is rotated is converted into an electric signal. In order to identify such damage on the rotator by utilizing the periodic characteristic of said electric signal, a peak detector is provided for detecting a peak value of said electric signal, holding the detected peak value for a fixed period, and being reset to a base level by a reset signal.

3 Claims, 8 Drawing Figures

CASE HAVING NO DAMAGE

CASE HAVING DAMAGE

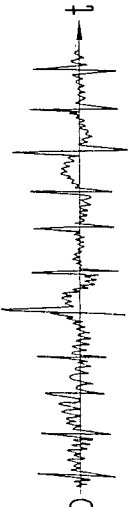
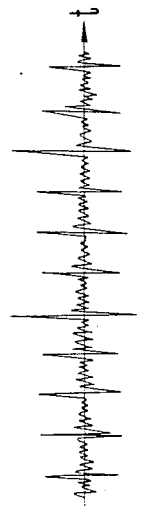
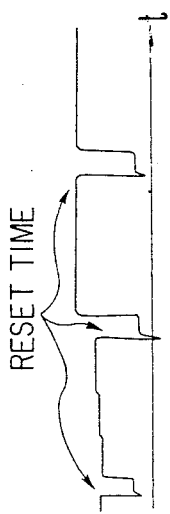
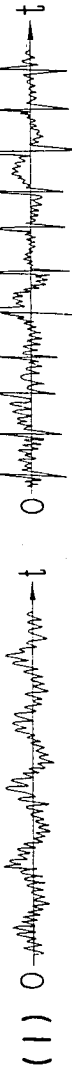
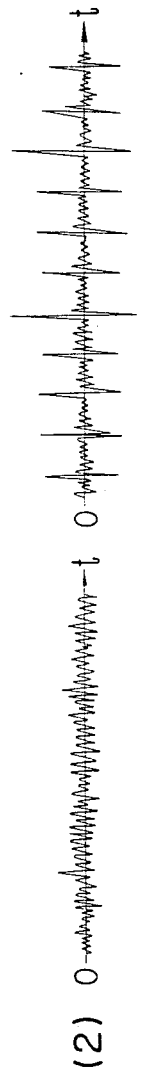
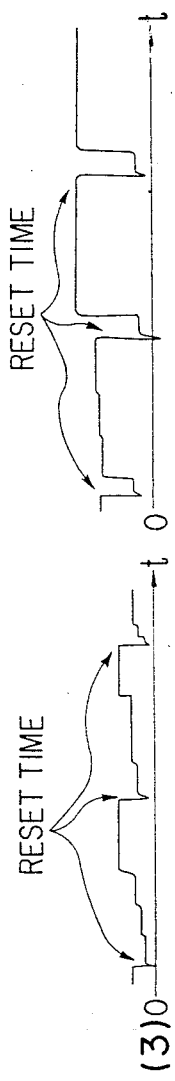
FIG. 6(A) CASE HAVING NO DAMAGE
FIG. 6(B) CASE HAVING DAMAGE

DEVICE FOR DETECTING DAMAGE ON ROTATORS

BACKGROUND OF THE INVENTION

1. Field of the Invention

This invention relates to a device for detecting damage on rotators or rotary bodies such as for example ball bearings having rolling elements, and more particularly to such rotator damage detecting device in which the mechanical vibration or sound produced periodically due to damage on a rotator when it is rotated is converted into an electric signal so as to identify such damage on the rotator by utilizing the periodic characteristic of said electric signal.

2. Description of the Prior Art

If a rotator such as for example a ball bearing has a flaw in its surface, mechanical vibration may be produced by such flaw when the rotator is rotated, and such mechanical vibration causes noise or other unfavorable results. Such flaws may be produced in the course of manufacture of the rotator or may develop from a dent or flaking which results from fatigue of the rotator in use.

Recently, more and more high-degree precision of the rotators such as above-mentioned is requested in certain fields or their use, and in order to meet such request, high-degree techniques for check and evaluation of the products are necessitated.

Heretofore, quality check of for example the ball bearings has been practiced by rotating the inner race, outer race and balls of each bearing relative to each other and measuring oscillation produced during rotation of the bearings. In a certain type of conventional detecting device, there is used a vibration pick-up for converting mechanical oscillation of the bearing into an electric signal and the output signal is frequency-discriminated to sort out the defectives according to the frequency ranges. However, since the defectives result not only from such flaws but also from other causes such as mixing of alien matters into grease, it is impossible to detect the flaws alone by such frequency discrimination method, and hence generally additional work is necessitated for further classifying the defectives by their types for post-treatments, thus making it hardly attainable to rationalize the working process.

In still another known checking device, it is attempted to find out the flaws or other damage by detecting the impulsive oscillation which is produced when the bearing is damaged by using a vibration pick-up and measuring the peak values of the electric signal produced therefrom. There are known roughly two types of methods for measuring such peak values. In one of such methods, the maximum peak voltages are retained substantially and the highest peak value thereof is measured by keeping it static. According to another method, the value of the signal voltage close to the envelope is measured by a peak detection circuit adapted with a suitable discharge time constant.

These method, however, have the following defects. That is, in the case of the former method, since the peak values resulting from sudden impulsive vibration caused by external disturbance or from electric noise are also retained, it is sometimes found hard to distinguish between such peak values and the ones associated with damage on the bearing, while in the latter method, it may become impossible to follow up the impulse signal produced from damage when the discharge time constant is short, making it impossible to measure the correct peak values, and when the time constant is long, the same problem as in the case of the former method arises.

SUMMARY OF THE INVENTION

It is therefore an object of the present invention to provide a novel damage detecting device which is capable of detecting flaws on rotators with high accuracy and with ease.

It is another object of the present invention to provide a damage detecting device which can detect damage on bearings with high accuracy and which is hardly influenced by oscillation caused by disturbance or electric noise.

According to the prominent features of the present invention, mechanical oscillation or sound produced when a subject rotator is rotating is converted into an electric signal and the peak values of this electric signal are detected, then retained for a certain fixed period of time and thereafter reset to zero, this being followed by the next round of peak detection, retention thereof for a fixed period of time and resetting to zero, with this cycle of operations being repeated at least twice during one period of the impulsive oscillation due to damage of the rotator. The period of the impulsive oscillation is, of course, dependent upon the rate of rotation of the rotator. The output signal from the peak detector is extracted as an AC component by removing the DC level by a band-pass filter, thus allowing detection of flaw on the rotator. Also, since the size of the flaw is proportional to the amplitude of said AC signal, it is possible not only to merely identify the flaw but also to determine the size of such flaw with high accuracy.

Further, according to the present invention, since detection of the peak values of said electric signal is made for each period of the impulsive oscillation, there is no possibility that the signal component derived from the presence of flaw be affected by said AC component in the substantial portion of the process owing to the false signal produced by mixing of a momentary noise component caused by factors, such as disturbance, not related with the flaw on the rotator. It is therefore possible to prevent false detection of flaw.

According to still another feature of the present invention, mechanical oscillation produced when a bearing is rotated is converted into an electric signal and the peak values of this electric signal are detected successively and its maximum value is retained for a fixed period of time and thereafter reset to an instantaneous value of the electric signal at the time of resetting. Then, again the next series of peak values are detected successively and its maximum value is retained for a fixed period of time and thereafter reset to an instantaneous value of the signal at the time of resetting, with the above-said operations being repeated cyclically. The period of said cycle of operations is set to be several times longer than the period of generation of the impulsive oscillation produced by the flaw on the bearing. This output signal is fed into a smoothing integrator to extract a means value, and this value is kept under observation to detect the flaw, if any, on the bearing in the early phase of such flaw. Also, since the degree of damage is generally in proportional relation with the size of the output signal from said integrator, it is possible not only to detect the damage but also to determine the degree of such damage.

According to still another feature of the present invention, detection of the peak values of said electric signal is made at every reset interval set to a desired period and the mean value of these peak values is obtained from the integration circuit, so that even if instantaneous noise caused by disturbance or other factors other than the damage on the bearing is mixed, the measured value is little affected. This makes it possible to prevent erroneous detection of damage. Also, if the reset interval in detection of the peak values is set at a proper period, it is possible to measure the values of bearing oscillation with high accuracy regardless of the time constant of the integration circuit. This allows high-accuracy detection of damage on the bearing.

The other objects, features and effects of the present invention will be understood from the following detailed description of some preferred embodiments of the invention when taken in conjunction with the accompanying drawings.

BRIEF DESCRIPTION OF THE DRAWINGS

FIG. 6 shows output wave-form diagrams of the principal parts in the rotator damage detecting device shown in a block diagram in FIG. 5.

DESCRIPTION OF THE PREFERRED EMBODIMENTS

Figure 1:
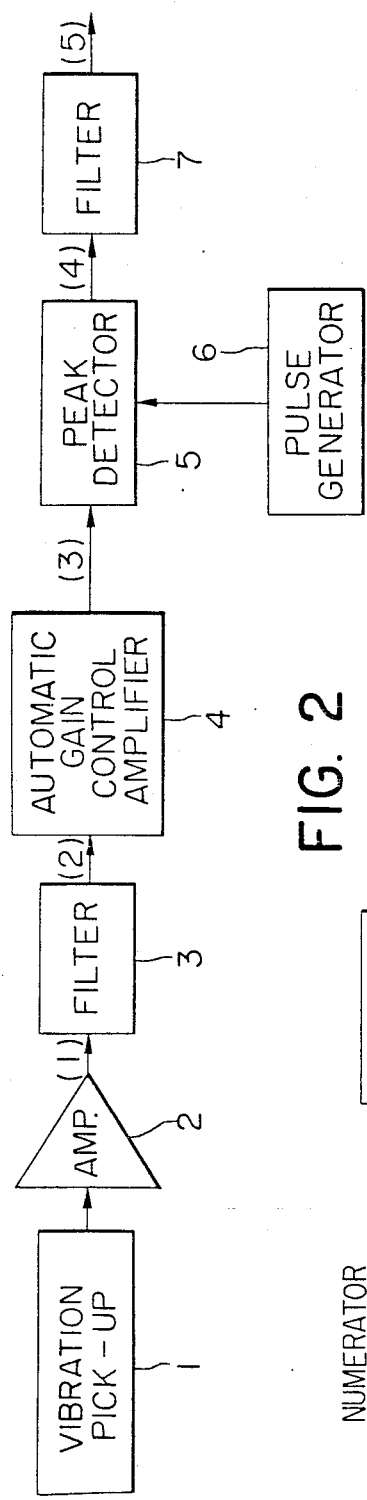
FIG. 1 is a block diagram showing an embodiment of the rotator damage detecting device according to the present invention.
Figure 4A:
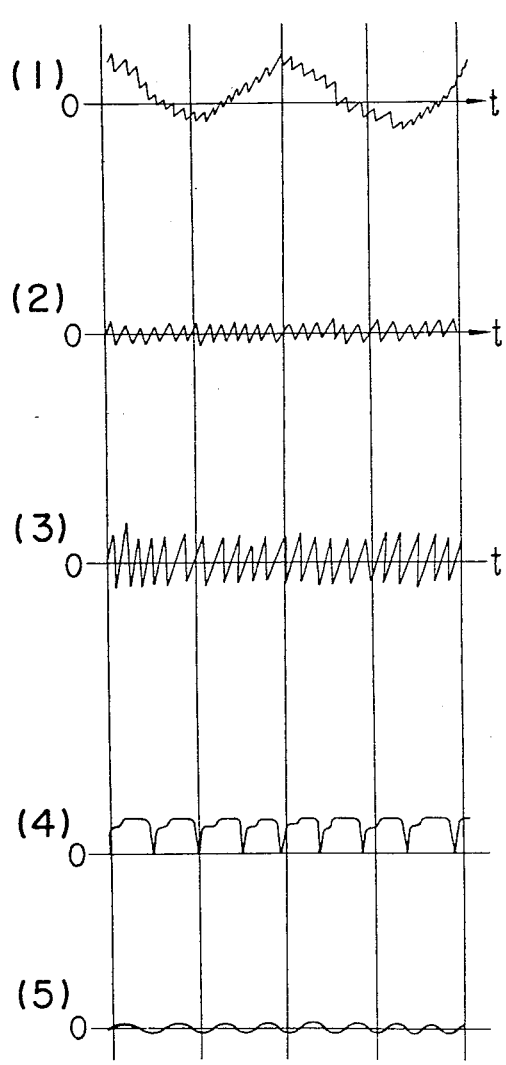
FIG. 4 shows output wave-form diagrams of the principal parts in the rotator damage detecting device shown in a block diagram in FIG. 1.
Figure 4B:
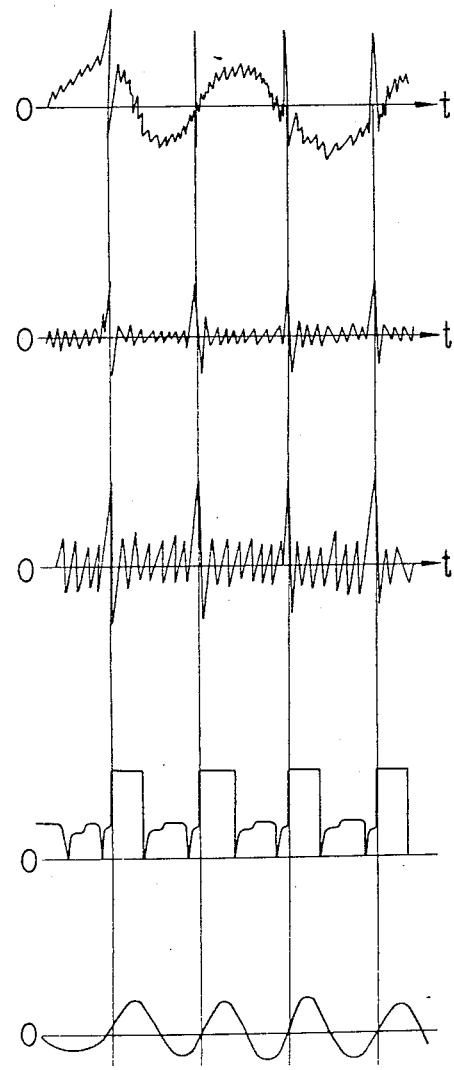

Referring to FIG. 1, reference numeral 1 designates a vibration pick-up or a microphone whereby the mechanical oscillation or sound of a rotator is converted into an electric signal, and the output signal thereof is amplified to a proper level by an amplifier 2. The output wave form of the amplifier in this case is shown in (1) in FIG. 4. The wave forms shown on the left side of FIG. 4, represented by (A), are the ones which appear in case no damage is present on the rotator, and those on the right side, represented by (B), are the ones which appear in case the rotator has damage on its surface.

The output of said amplifier 2 is applied to an automatic gain control amplifier 4 after passing a band-pass filter 3 wherein the signal component unnecessary for the signal processing, that is, the low frequency component, is removed. The wave form of the output signal from said filter 3 is shown in (2) in FIG. 4. The band-pass filter used in this invention is preferably a Bessel function type filter whose damping factor is higher than 24 dB/octave, and this type of band-pass filter can be used in any embodiment of the present invention described hereinbelow.

Figure 2:
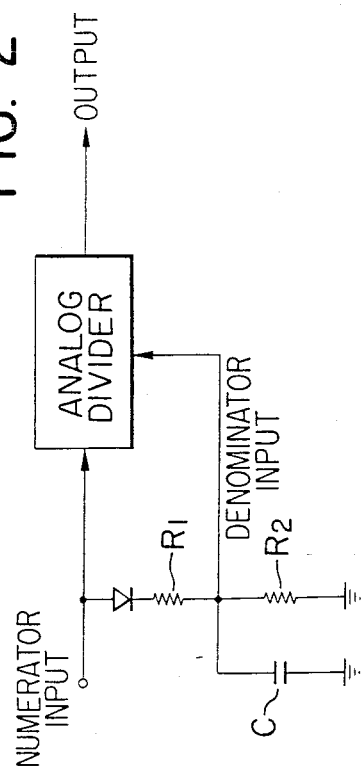
FIG. 2 is a circuit diagram showing the arrangement of the automatic gain control amplifier shown in the block diagram of FIG. 1.
Figure 3:
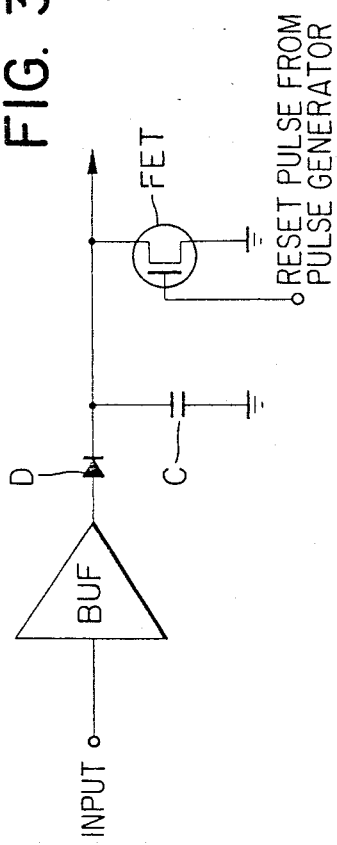
FIG. 3 is a circuit diagram showing the arrangement of the peak detector shown in the block diagram of FIG. 1.

In the automatic gain control amplifier 4, the gain of the amplifier is controlled so that signals of a constant level can be obtained. This permits evaluation of the damage always with a same criterion regardless of the oscillation amplitude which varies depending on the pick-up mounted position or difference in size of the bearings. Said automatic gain control amplifier may be of a generally known construction. FIG. 2 shows an example where an analog divider is used. This analog divider may be for example DIVIDER MODULE "Model 4094/15c" by Burr-Brown Inc. of the U.S. or the equivalent. The output of said automatic gain control amplifier 4 is shown in (3) in FIG. 4. This output is then applied to a peak detector 5 where the peak value of the input signal is detected and the DC level proportional thereto is retained for fixed period of time, and thence the DC level which has been retained by the reset pulse is instantaneously reset to the zero level, this being immediately followed by start of detection of the next peak value. Said reset pulse is given from a reset pulse generator 6. What is to be noted here is that the reset is accomplished instantaneously and that the pulse repetition rate is such that the interval from one reset to the next is set to be shorter than the interval of generation of peak values due to the damage on the rotator. The output wave form of said peak detector 5 is shown in (4) in FIG. 4. This peak detector can be constituted from a combination of a buffer, a contraflow preventive diode, a capacitor and a discharging field effect transistor FET as shown in FIG. 3, but it is possible to use Peak Detector Module 4084/25 (product number) by Burr-Brown Inc. In the band-pass filter 7 of the next stage, the impulsive noise produced at the time of resetting and possessed by the output of said detector 5 is eliminated together with the DC component to extract the AC component alone. Therefore, no such AC component appears in case the rotator has no damage as shown by (A) in (5) of FIG. 4, but the AC component itself appears in case the rotator has damage as shown by (B).

The size of the AC component thus obtained is proportional to the size of the damage on the rotator. Therefore, means may be incorporated for indicating this AC component by an AC meter having a long time constant, or for DC-converting said component by an AC-DC converter and then applying it to a comparator which compares the obtained value with a predetermined reference value and judges whether the rotator is normal or abnormal.

Figure 5:
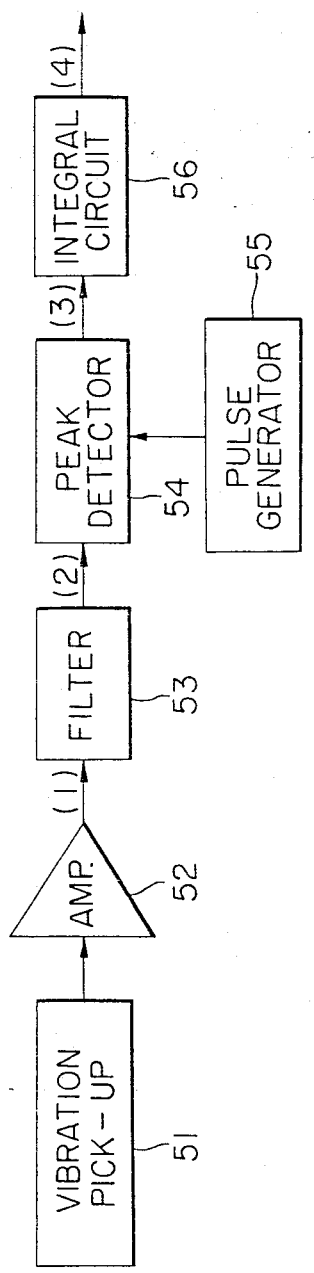
FIG. 5 is a block diagram showing another embodiment of the rotator damage detecting device according to the present invention.

Referring now to FIG. 5, there is shown another preferred embodiment of rotator damage detecting device according to the present invention.

In FIG. 5, numeral 51 designates a vibration pick-up whereby the mechanical oscillation of the bearing is converted into an electric signal, and the output signal therefrom is amplified to a proper level by an amplifier 52. The output wave form of the amplifier in this case is shown in (1) in FIG. 6. The wave forms shown on the left side of FIG. 6, represented by (A), are the ones which appear in case the bearing has no damage, and those shown on the right side, represented by (B), are the ones which appear in case the bearing has damage.

The output of said amplifier 52 is applied to a peak detector 54 after passing a band-pass filter 53 where the frequency component unnecessary for the signal processing is eliminated. The signal wave form of the output of the filter 53 is shown in (2) in FIG. 6. Said peak detector 54 detects the peak values of the input signal, and the DC level proportional thereto is retained for a certain fixed period of time, and thereafter the DC level which has been retained by the reset pulse is instantaneously reset to the instantaneous value of the input signal at the time of resetting, which is immediately followed by detection of the next peak value. Said reset pulse is given from a reset pulse generator 55. What is to be noted here is that the resetting is made instantaneously and that the pulse repetition rate is such that the interval from one reset to the next is set to be several times longer than the period of generation of impulsive oscillation produced due to presence of the damage on the bearing. The output wave form of said peak detector 54 is shown in (3) in FIG. 6.

Said peak detector 54 may be for example Peak Detector Module 4084/25 by Burr-Brown Inc. of the U.S. The integration circuit 56 of the next stage is adapted for smoothing the output signal of said peak detector 54, and the integration time constant is selected to be sufficiently longer than the afore-mentioned reset interval. This integration circuit 56 may be an ordinary RC integration circuit consisting of a resistance R and a capacitor C.

Therefore, in case the bearing has no damage as shown by (A) in (4) of FIG. 6, the output voltage of said integration circuit 56 stays at the DC level proportional to the stationary oscillation amplitude of the bearing. While in case the bearing suffers damage as shown by (B) in (4) of FIG. 6, the DC level proportional to the peak value of impulsive oscillation produced by the damage becomes the output voltage of the integration circuit 56, so that the voltage value becomes far greater than in case the bearing has no damage.

Since the output voltage thus obtained is in a proportional relation with the degree of damage of the bearing, means may be incorporated for indicating such output voltage by a meter or for operating an alarm or relay when said output voltage has exceeded the setting value, so as to allow early detection of damage on the bearing.

I claim:

1. A device for detecting damage on a rotator by converting into electric signals the mechanical oscillation or sound produced when sai rotator is rotated, and evaluating the amplitude of the electric signals originating from the presence of damage on the rotator manifested as an impulsive oscillation having a period dependent upon the rate of rotation of said rotator, said device comprising:
    a peak detector for detecting the peak value of said electric signals and holding that value as a DC level,
    a reset pulse generator for generating reset pulses having a predetermined pulse repetition rate to reset said peak detector at a predetermined time interval, the repetition rate of the reset pulses being predetermined so that said peak detector repeats at least twice the cycle of peak detecting, holding sand resetting during one period of said impulsive oscillation, and
    means for deriving an output signal from said peak detector.

2. A device in accordance with claim 1, further comprising a band-pass filter for eliminating the DC output component from said peak detector output signal and extracting the AC component alone, whereby the damage, if any, on the rotator is detected according to the presence or absence of said AC component.

3. A device for detecting damage on rotator by converting into electric signals the mechanical oscillation or sound produced when said rotator is rotated, and evaluating the amplitude of the electric signals originating from the presence of damage on the rotator manifested as an impulsive oscillation having a period dependent upon the rate of rotation of said rotator, said device comprising:
    a peak detector for detecting the peak value of said electric signals and holding that value as a DC level,
    a reset pulse generator for generating reset pulse having a predetermined pulse repetition rate to reset said peak detector at a predetermined time interval, the repetition rate of the reset pulses being predetermined so that the period of the cycle of peak detecting, holding and resetting is several times longer than the period of said impulsive oscillation,
    means for deriving an output signal from said peak detector, and
    an integration circuit for smoothing said output signal, whereby the presence and degree of the damage on the rotator are detected according to the amount of a DC output voltage of said integration circuit.

* * * * *